United States Patent
Myntti

(10) Patent No.: US 11,723,361 B2
(45) Date of Patent: *Aug. 15, 2023

(54) ANTIMICROBIAL COMPOSITION HAVING EFFICACY AGAINST ENDOSPORES

(71) Applicant: Next Science IP Holdings Pty Ltd, Chatswood (AU)

(72) Inventor: Matthew F. Myntti, Ponte Vedra Beach, FL (US)

(73) Assignee: Next Science IP Holdings Pty Ltd, Chatswood (AU)

( * ) Notice: Subject to any disclaimer, the term of this patent is extended or adjusted under 35 U.S.C. 154(b) by 322 days.

This patent is subject to a terminal disclaimer.

(21) Appl. No.: 17/092,260

(22) Filed: Nov. 7, 2020

(65) Prior Publication Data

US 2021/0176987 A1 Jun. 17, 2021

Related U.S. Application Data

(63) Continuation of application No. 15/745,094, filed as application No. PCT/US2016/042780 on Jul. 18, 2016, now Pat. No. 10,827,750.

(60) Provisional application No. 62/194,141, filed on Jul. 17, 2015, provisional application No. 62/194,210, filed on Jul. 18, 2015.

(51) Int. Cl.
| | | |
|---|---|---|
| A01N 37/16 | (2006.01) | |
| A01N 25/04 | (2006.01) | |
| A01N 25/30 | (2006.01) | |
| A01N 59/00 | (2006.01) | |
| A61L 2/18 | (2006.01) | |

(52) U.S. Cl.
CPC ............ *A01N 37/16* (2013.01); *A01N 25/04* (2013.01); *A01N 25/30* (2013.01); *A01N 59/00* (2013.01); *A61L 2/18* (2013.01); *A61L 2202/23* (2013.01); *A61L 2202/24* (2013.01); *A61L 2202/25* (2013.01)

(58) Field of Classification Search
CPC .. A61L 2/00; A61L 2/18; A01N 37/16; A01N 25/04; A01N 59/00
USPC ............ 422/28; 252/186.4; 516/15; 510/110
See application file for complete search history.

(56) References Cited

U.S. PATENT DOCUMENTS

| | | | |
|---|---|---|---|
| 5,186,946 A | 2/1993 | Vallieres | |
| 6,514,509 B2 | 2/2003 | Tabasso | |
| 10,477,860 B2 | 11/2019 | Myntti | |
| 10,827,750 B2* | 11/2020 | Myntti | A01N 25/30 |
| 2002/0004057 A1 | 1/2002 | Tabasso | |
| 2013/0272922 A1* | 10/2013 | Myntti | A01N 41/04 514/642 |
| 2015/0086647 A1 | 3/2015 | Lakaye et al. | |

FOREIGN PATENT DOCUMENTS

| | | |
|---|---|---|
| GB | 1571357 | 7/1980 |
| JP | S61-286306 A | 12/1986 |
| JP | 2005-154551 A | 9/2010 |
| WO | 2003028429 A2 | 4/2003 |

OTHER PUBLICATIONS

JPO examination report in JP appl. No. 2018-521500, dated Aug. 24, 2020.
EPO examination report in EP appl. No. 16857926.6, dated Jul. 6, 2020.
EPO extended search report in EP appl. No. 16857926.6, dated Jul. 6, 2020.
CIPO examination report in CA appl. No. 2992543, dated Aug. 26, 2022.

* cited by examiner

*Primary Examiner* — Monzer R Chorbaji
(74) *Attorney, Agent, or Firm* — Element IP, PLC; David G. Burleson

(57) ABSTRACT

A sporicidal composition has a moderately low pH and includes at least one oxidizing acid and the dissociation product of at least one inorganic oxidizing agent. Very high effective solute concentrations can enhance the efficacy of the composition. Embodiments of the composition can be applied to a surface and allowed to absorb into the endospore, ultimately killing at least some of those bacteria in mature endospore form. The surface being treated can be an inanimate surface, particularly a hard surface, or a medical device.

20 Claims, No Drawings

ANTIMICROBIAL COMPOSITION HAVING EFFICACY AGAINST ENDOSPORES

CROSS REFERENCE TO RELATED APPLICATIONS

This application is a continuation of U.S. application Ser. No. 15/745,094, which issued as U.S. Pat. No. 10,827,750 on 10 Nov. 2020, which is a national stage entry of international appl. no. PCT/US2016/042780, filed 18 Jul. 2016, which claims the benefit of U.S. provisional patent application Nos. 62/194,141 and 62/194,210, filed 17 Jul. 2015 and 18 Jul. 2015, respectively, the disclosures of which are incorporated herein by reference.

BACKGROUND INFORMATION

Unlike a true spore, an endospore is not an offspring of another living organism. Nevertheless, the terms "spore" and "endospore" are used interchangeably hereinthroughout.

A vegetative bacterium is one which can grow, feed and reproduce. When nutrients become scarce, certain vegetative bacteria begin a process referred to as "sporulation," where they take on a reduced, dormant form which permits them to survive without nutrients and gives them resistance to UV radiation, desiccation, elevated temperatures, extreme freezing and chemical disinfectants. Soon after environmental conditions return to being favorable for vegetative growth, such bacteria can exit their dormant state ("spore germination") with the spore core rehydrating, the cortex hydrolyzing, the coat being shed and, ultimately, DNA replication being initiated. For additional information on these complex processes, the interested reader is directed to any of a variety of texts such as, for example, J. C. Pommerville, *Fundamentals of Microbiology*, 10th ed. (Jones & Bartlett Learning; Burlington, Mass.).

At the outset of the sporulation step, a vegetative bacterium called a "mother cell" makes a copy of its DNA and then forms a membrane around the new copy of DNA, with the section of the cell having the copied DNA completely surrounded by a membrane being referred to as a "forespore." The next morphological stage of sporulation is "engulfment" of the forespore by its mother cell, a process that is analogous to phagocytosis; when engulfment is complete, the forespore is entirely surrounded by its inner and outer membranes and free in the mother cell cytoplasm. Around this core of the spore is assembled a series of protective structures, completion of which results in a mature endospore, which is released after the mother cell is broken apart.

Endospores have a multi-layer structure, all of which protect the nucleus. The nucleus is protected by a number of layers, set forth below in Table 1 in order from inside-to-outside:

TABLE 1

| Layer | Description |
| --- | --- |
| (1) core | protoplast that contains RNA, DNA, dipicolinic acid, low molecular weight basic proteins, and various minerals such as Ca, K, Mn and P |
| (2) cortical (outer) membrane | non-crosslinked or lightly crosslinked peptidoglycan-containing layer that develops into cell wall during germination |
| (3) cortex | peptidoglycan and manuronic acid residues |
| (4) inner spore coat | primarily acidic polypeptides |

TABLE 1-continued

| Layer | Description |
| --- | --- |
| (5) outer spore coat | primarily protein with some carbohydrates and lipids and, in the case of *C. difficile*, a large amount of phosphorus |

The inner spore coat is soluble in alkali solutions, but the outer spore coat is resistant to hydrolysis from alkalis, probably due in significant part to its numerous disulfide (—S—S—) linkages.

Spores are extremely difficult to eradicate and are involved in the spread of diseases such as *Clostridium difficile* (*C. diff*) infection and anthrax.

*C. difficile* is a Gram-positive, spore-forming bacterium often found in healthcare facilities and is the cause of antibiotic-associated diarrhea. *C. difficile* infection is a growing problem, affecting hundreds of thousands of people each year, killing a significant portion of those affected. *C. difficile* spores are resistant to most routine surface cleaning methods, remaining viable in the environment for long periods of time.

Anthrax is an acute, usually lethal, disease that affects both humans and animals, caused by the bacterium *Bacillus anthracis* (*B. anthracis*), which spores can be produced in vitro and used as a biological weapon. Anthrax does not spread directly from one infected animal or person to another, instead being spread by spores.

Sporostatic compounds are not sporicidal, i.e., they do not kill spores; instead, they inhibit germination of spores or cause germinated spores to grow abnormally. Spores can survive exposure to these compounds and then grow after sporostatic compounds no longer are present. Sporostatic compounds include phenols and cresols, organic acids and esters, alcohols, quaternary ammonia compounds, biguanides, and organomercury compounds. Certain of these sporostatic compounds can be marginally sporicidal at high concentrations; see, e.g., A. D. Russell, "Bacterial Spores and Chemical Sporicidal Agents," *Clinical Microbiology Reviews*, pp. 99-119 (1990)) for the relative concentrations of certain sporostatic compounds needed to achieve any sporicidal efficacy.

Commonly employed spore treatment options include aldehydes, particularly gluteraldehyde and formaldehyde; chlorine-releasing agents including $Cl_2$, sodium hypochlorite, calcium hypochlorite, and chlorine reducing agents such as dichloroisocyanurate; iodine and iodophors; peroxygens including hydrogen peroxide and peracetic acid; gases such as ethylene oxide, propylene oxide and ozone; and β-propiolactone. The mechanisms of their activities against spores are not particularly well understood although, in all cases, the activity is rate-limited by the permeation of the active molecule(s) through the protective layers of the spore. This need to penetrate the various layers of protection means that spores must be exposed to these products for long periods of time at high concentrations.

U.S. Pat. Nos. 8,940,792 and 9,314,017 as well as U.S. Pat. Publ. Nos. 2010/0086576, 2013/0272922, 2013/0079407 and 2016/0073628 describe antimicrobial compositions and various uses therefor. The core and cortex (including cortical membrane) of a spore are susceptible to dissolution and lysis by the types of high osmolarity compositions described in these documents. However, such compositions have not been found to be particularly effective against spores, likely due to a limited ability to break down and then penetrate the outer and inner spore coats.

That which remains desirable is a composition that is capable of penetrating the various defenses of endospores and killing bacteria therein. Such a composition preferably is effective against endospores of bacteria such as of *C. difficile* and *B. anthracis* while not presenting toxicity concerns toward humans who handle or contact it.

SUMMARY

In one aspect is provided a composition that can kill a variety of endospore-forming bacteria while in mature endospore form. Embodiments of the composition are effective against the various defenses of bacteria in endospore form, specifically, disulfide bonds can be cleaved, intrinsic hydrophobicity can be overcome, peptidoglycan can be disrupted, and the core and cortical membrane can be lysed.

The composition is acidic but has a pH≥1.5 and includes solvent and solute components, the latter including at least one oxidizing acid and the dissociation product of at least one electrolyte oxidizing agent. In certain embodiments, the composition also can include one or more of an organic liquid, a wetting agent (particularly an ionic surfactant), and any of a variety of non-oxidizing electrolytes. Advantageously, the composition need not include an active antimicrobial agent to be sporicidal.

The composition has an effective solute concentration of at least 1.0 Osm/L, typically at least 1.5 Osm/L and often even higher, up to the solubility limit of the solute component in the solvent component.

Also provided is a method of treating a surface. The method involves applying an embodiment of the foregoing composition to the surface and permitting the composition to be absorbed into the endospore and to kill at least some of those bacteria in mature endospore form. The surface being treated can be an inanimate surface, particularly a hard surface, and advantageously a hard surface in a healthcare facility.

Embodiments of the composition, when used in conjunction with tests such as ASTM standard E2197-11 and AOAC Official Method 966.04 can provide positive (passing) results within commercially relevant timeframes. For example, janitorial-type disinfecting treatment of (inanimate) hard surfaces can be effected in less than 20 minutes, while sterilizing treatment of medical instruments can be effected in less than 4 hours.

Other aspects of the invention will be apparent to the ordinarily skilled artisan from the detailed description that follows. To assist in understanding that description, certain definitions are provided immediately below, and these are intended to apply throughout unless the surrounding text explicitly indicates a contrary intention:

"comprising" means including, but not be limited to, the listed ingredients or steps;

"consisting of" means including only the listed ingredients (or steps) and minor amounts of inactive additives or adjuvants;

"consisting essentially of" means including only the listed ingredients (or steps), minor amounts (less than 5%, 4%, 3%, 2%, 1%, 0.5%, 0.25%, or 0.1%) of other ingredients that supplement sporicidal activity and/or provide a secondary effect (e.g., antifogging, soil removal, etc.) that is desirable in view of the intended end use, and/or inactive additives or adjuvants;

"polyacid" means a compound having at least two carboxyl groups and specifically includes dicarboxylic acids, tricarboxylic acids, etc.;

"pH" means the negative value of the base 10 logarithm of [H+] as determined by an acceptably reliable measurement method such as a properly calibrated pH meter, titration curve against a known standard, or the like;

"p$K_a$" means the negative value of the base 10 logarithm of a particular compound's acid dissociation constant;

"$E^o_{red}$" means the standard voltage for a reduction half-reaction in water at 25° C.;

"buffer" means a compound or mixture of compounds having an ability to maintain the pH of a solution to which it is added within relatively narrow limits;

"buffer precursor" means a compound that, when added to a mixture containing an acid, results in a buffer;

"electrolyte" means a compound that exhibits some dissociation when added to water;

"non-oxidizing electrolyte" means an electrolyte other than one that can act as an oxidizing agent;

"benzalkonium chloride" refers to any compound defined by the following general formula

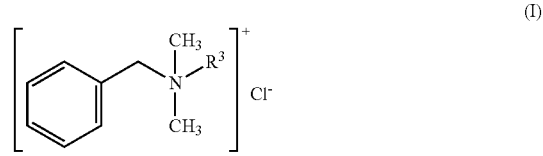

where $R^3$ is a $C_8$-$C_{18}$ alkyl group, or any mixture of such compounds;

"effective solute concentration" is a measurement of the colligative property resulting from the number of moles of molecules (from nonelectrolyte) or ions (from electrolytes) present in a given volume solution, often presented in units of osmoles per liter;

"$\delta_p$" is the dipolar intermolecular force Hansen Solubility Parameter (HSP), with the value for a solution or mixture of solvents being calculated by $$\delta_p = \sum_{i=1}^{n} (\delta_{di} \times x_{di}) \tag{I}$$

where $\delta_{di}$ is the energy from dipolar intermolecular force for solvent component i, $x_{di}$ is the percentage of solvent component i relative to the total amount of solvent components, and n is the total number of solvent components;

"oxyacid" means a mineral acid that contains oxygen;

"substituted" means containing a heteroatom or functionality (e.g., hydrocarbyl group) that does not interfere with the intended purpose of the group in question;

"microbe" means any type of microorganism including, but not limited to, bacteria, viruses, fungi, viroids, prions, and the like;

"antimicrobial agent" means a substance having the ability to cause greater than a 90% (1 log) reduction in the number of one or more microbes;

"active antimicrobial agent" means an antimicrobial agent that is effective only or primarily during the active parts of the lifecycle, e.g., cell division, of a microbe;

"germicide" means a substance that is lethal to one or more types of harmful microorganisms;

"disinfectant" means a substance that is lethal to one or more types of bacteria;

"high level disinfectant" means a disinfectant that is capable of killing all bacteria except for small amounts of bacteria in endospore form;

"sterilant" means a substance capable of eliminating at least a 6 log (99.9999%) reduction of all microbes, regardless of form;

"contact time" means the amount of time that a composition is allowed to contact a surface and/or an endospore on such a surface;

"hard surface" means any surface that is non-porous to fluids and, in most cases, non-deformable; and "healthcare" means involved in or connected with the maintenance or restoration of the health of the body or mind.

Throughout this document, unless the surrounding text explicitly indicates a contrary intention, all values given in the form of percentages are w/v, i.e., grams of solute per liter of composition. The relevant portion(s) of any specifically referenced patent and/or published patent application are incorporated herein by reference.

DETAILED DESCRIPTION OF ILLUSTRATIVE EMBODIMENTS

The sporicidal composition is described first in terms of its properties and components, many of which are widely available and relatively inexpensive, and then in terms of certain uses.

The solvent component of the composition typically includes a significant amount of water. Relative to its overall volume, a composition often includes up to 20%, 25%, 30%, 33%, 35%, 40%, 45%, 50%, or even 55% (all v/v). On a per liter basis, a composition often includes from ~50 to ~500 mL, commonly from ~75 to ~475 mL, more commonly from ~100 to ~450 mL, usually from ~125 to ~425 mL, typically from ~150 to ~400 mL, and most typically 250±50 mL water. The water need not be specially treated (e.g., distilled and/or deionized), although preference certainly can be given to water that does not interfere with the intended antimicrobial effect of the composition.

The solvent component of the composition often includes at least one organic liquid, and, in some embodiments, preference is given to those organic liquids with $\delta_p$ values lower than that of water ($\delta_p \sim 16.0$ MPa$^{1/2}$). Where at least one organic liquid is present in the solvent component, the $\delta_p$ value of the overall solvent component generally is less than 16.0, no more than 15.6, no more than 15.2, no more than 15.0, no more than 14.6 or no more than 14.0 MPa$^{1/2}$. In some embodiments, the $\delta_p$ value of the overall solvent component can range from 13.1 to 15.7 MPa$^{1/2}$, from 13.3 to 15.6 MPa$^{1/2}$, from 13.5 to 15.5 MPa$^{1/2}$, and even from 13.7 to 15.4 MPa$^{1/2}$.

The organic liquid(s) often is/are present at concentrations of up to 60%, commonly 5 to 50%, more commonly 10 to 45%, even more commonly 15 to 40%, and typically 20 to 35% (all w/v, based on total volume of solvent component).

The amount of a given organic liquid (or mixture of organic liquids) to be added to water can be calculated using formula (I) if a targeted $\delta_p$ value is known. Similarly, a projected $\delta_p$ value can be calculated using formula (I) if the amount of organic liquid(s) and their individual $\delta_p$ values are known.

The solvent component can consist of, or consist essentially of, only water or only one or more organic liquids, with preference being given to mixtures of species of the same genus of organic liquids, e.g., two ethers or two alcohols rather than one ether and one alcohol. In certain preferred embodiments, the solvent component can consist of, or consist essentially of, water and an organic liquid, preferably one having a $\delta_p$ value less than 15.5 MPa$^{1/2}$. In yet other embodiments, the solvent component can consist of, or consist essentially of, water and two or more organic liquids, with the resulting solvent component having $\delta_p$ value that can be calculated using formula (I); again, preference is given to mixtures of species of the same genus of organic liquids, e.g., two ethers or two alcohols rather than one ether and one alcohol.

With respect to organic liquids that can be employed in the solvent component, those which are miscible with one another and/or water are preferred. Non-limiting examples of potentially useful organic liquids include ketones such as acetone, methyl butyl ketone, methyl ethyl ketone and chloroacetone; acetates such as amyl acetate, ethyl acetate and methyl acetate; (meth)acrylates and derivatives such as acrylamide, lauryl methacrylate and acrylonitrile; aryl compounds such as benzene, chlorobenzene, fluorobenzene, toluene, xylene, aniline and phenol; aliphatic alkanes such as pentane, isopentane, hexane, heptane and decane; halogenated alkanes such as chloroform, methylene dichloride, chloroethane and tetrachloroethylene; cyclic alkanes such as cyclopentane and cyclohexane; and polyols such as ethylene glycol, diethylene glycol, propylene glycol, hexylene glycol, and glycerol. When selecting such organic liquids for use in the solvent component of the composition, possible considerations include avoiding those which contain a functional group that will react with the acid(s) and optionally, salt(s) employed in the composition and favoring those which possess higher regulatory pre-approval limits.

Preferred organic liquids include ethers and alcohols due to their low tissue toxicity and environmentally friendliness. These can be added at concentrations up to the solubility limit of the other ingredients in the composition.

Ether-based liquids that can be used in the solvent component include those defined by the following general formula $$R^1(CH_2)_xO—R^2—[O(CH_2)_z]_yZ \quad (II)$$

where x is an integer of from 0 to 20 (optionally including, where 2≤x≤20, one or more points of ethylenic unsaturation), y is 0 or 1, z is an integer of from 1 to 4, $R^2$ is a $C_1$-$C_6$ linear or branched alkylene group, $R^1$ is a methyl, isopropyl or phenyl group, and Z is a hydroxyl or methoxy group. Non-limiting examples of glycol ethers (formula (II) compounds where Z is OH) that can be used in the solvent component are set forth below in Table 2.

TABLE 2

Representative glycol ethers, with formula (II) variables and $\delta_p$ values

|  | $R^1$ | x | $R^2$ | y | z | $\sim \delta_p$ (MPa$^{1/2}$) |
|---|---|---|---|---|---|---|
| ethylene glycol monomethyl ether | $CH_3$ | 0 | $(CH_2)_2$ | 0 | — | 9.2 |
| ethylene glycol monoethyl ether | $CH_3$ | 1 | $(CH_2)_2$ | 0 | — | 9.2 |

TABLE 2-continued

Representative glycol ethers, with formula (II) variables and $\delta_p$ values

|  | $R^1$ | x | $R^2$ | y | z | $\sim\delta_p$ (MPa$^{1/2}$) |
|---|---|---|---|---|---|---|
| ethylene glycol monopropyl ether | $CH_3$ | 2 | $(CH_2)_2$ | 0 | — | 8.2 |
| ethylene glycol monoisopropyl ether | $(CH_3)_2CH$ | 0 | $(CH_2)_2$ | 0 | — | 8.2 |
| ethylene glycol monobutyl ether | $CH_3$ | 3 | $(CH_2)_2$ | 0 | — | 5.1 |
| ethylene glycol monophenyl ether | $C_6H_5$ | 0 | $(CH_2)_2$ | 0 | — | 5.7 |
| ethylene glycol monobenzyl ether | $C_6H_5$ | 1 | $(CH_2)_2$ | 0 | — | 5.9 |
| diethylene glycol monomethyl ether | $CH_3$ | 0 | $(CH_2)_2$ | 1 | 2 | 7.8 |
| diethylene glycol monoethyl ether (DGME) | $CH_3$ | 1 | $(CH_2)_2$ | 1 | 2 | 9.2 |
| diethylene glycol mono-n-butyl ether | $CH_3$ | 3 | $(CH_2)_2$ | 1 | 2 | 7.0 |
| propylene glycol monobutyl ether | $CH_3$ | 3 | $(CH_2)_3$ | 0 | — | 4.5 |
| propylene glycol monoethyl ether | $CH_3$ | 1 | $(CH_2)_3$ | 0 | — | 6.5 |
| propylene glycol monoisobutyl ether | $(CH_3)_2CH$ | 1 | $(CH_2)_3$ | 0 | — | 4.7 |
| propylene glycol monoisopropyl ether | $(CH_3)_2CH$ | 0 | $(CH_2)_3$ | 0 | — | 6.1 |
| propylene glycol monomethyl ether | $CH_3$ | 0 | $CH_2CH(CH_3)$ | 0 | — | 6.3 |
| propylene glycol monophenyl ether | $C_6H_5$ | 0 | $CH_2CH(CH_3)$ | 0 | — | 5.3 |
| propylene glycol monopropyl ether (PGME) | $CH_3$ | 2 | $CH_2CH(CH_3)$ | 0 | — | 5.6 |
| triethylene glycol monomethyl ether | $CH_3$ | 0 | $(CH_2)_2$ | 2 | 2 | 7.6 |
| triethylene glycol monooleyl ether | $CH_3$ | 17* | $(CH_2)_2$ | 2 | 2 | 3.1 |

*includes unsaturation at the 9 position

Cyclic and $C_1$-$C_{16}$ acyclic (both linear and branched, both saturated and unsaturated) alcohols, optionally including one or more points of ethylenic unsaturation and/or one or more heteroatoms other than the alcohol oxygen such as a halogen atom, an amine nitrogen, and the like, can be employed as an organic liquid in the solvent component of the composition. Non-limiting examples of representative examples are compiled in the following table.

TABLE 3

Representative alcohols, with $\delta_p$ values

| | $\sim\delta_p$ (MPa$^{1/2}$) |
|---|---|
| 2-propenol | 10.8 |
| 1-butanol | 5.7 |
| t-butyl alcohol | 5.1 |
| 4-chlorobenzyl alcohol | 7.5 |
| cyclohexanol | 4.1 |
| 2-cyclopentenyl alcohol | 7.6 |
| 1-decanol | 10.0 |
| 2-decanol | 10.0 |
| 2,3-dichloropropanol | 9.2 |
| 2-ethyl-1-butanol | 4.3 |
| ethanol | 8.8 |
| 2-ethyl-hexanol | 3.3 |
| isooctyl alcohol | 7.3 |
| octanol | 3.3 |
| methanol | 12.3 |
| oleyl alcohol | 2.6 |
| 1-pentanol | 4.5 |
| 2-pentanol | 6.4 |
| 1-propanol | 6.8 |
| 2-propanol (IPA) | 6.1 |

For further information on organic liquid-containing solvent components, the interested reader is directed to U.S. Pat. Publ. No. 2016/0073628.

The composition is acidic, more particularly having a pH of no more than 4, and certain embodiments can have a pH of no more than 3.8, 3.7, 3.6, 3.5, 3.4, 3.3, 3.2, 3.1, 3.0, 2.9, 2.8, 2.7, 2.6, 2.5, 2.4, 2.3 or even 2.2. The composition has a pH of at least 1.5, generally at least 1.75, and typically at least 2.0. Ranges of pH values employing each of the lower limits in combination with each of the upper limits are envisioned. Embodiments of the composition can have pH values of 2.75±1.15, 2.70±1.05, 2.65±1.0, 2.60±0.75, 2.55±0.60, 2.50±0.55 and 2.45±0.45.

Acidity can be achieved by adding to the solvent component (or vice versa) one or more acids. Strong (mineral) acids such as HCl, $H_2SO_4$, $H_3PO_4$, $HNO_3$, $H_3BO_3$, and the like or organic acids, particularly organic polyacids, may be used. Examples of organic acids include monoprotic acids such as formic acid, acetic acid and substituted variants (e.g., hydroxyacetic acid, chloroacetic acid, dichloroacetic acid, phenylacetic acid, and the like), propanoic acid and substituted variants (e.g., lactic acid, pyruvic acid, and the like), any of a variety of benzoic acids (e.g., mandelic acid, chloromandelic acid, salicylic acid, and the like), glucuronic acid, and the like; diprotic acids such as oxalic acid and substituted variants (e.g., oxamic acid), butanedioic acid and substituted variants (e.g., malic acid, aspartic acid, tartaric acid, citramalic acid, and the like), pentanedioic acid and substituted variants (e.g., glutamic acid, 2-ketoglutaric acid, and the like), hexanedioic acid and substituted variants (e.g., mucic acid), butenedioic acid (both cis and trans isomers), iminodiacetic acid, phthalic acid, and the like; triprotic acids such as citric acid, 2-methylpropane-1,2,3-tricarboxylic acid, benzenetricarboxylic acid, nitrilotriacetic acid, and the like; tetraprotic acids such as prehnitic acid, pyromellitic acid, and the like; and even higher degree acids (e.g., penta-, hexa-, heptaprotic, etc.). Where a tri-, tetra-, or higher acid is used, one or more of the carboxyl protons can be replaced by cationic atoms or groups (e.g., alkali metal ions), which can be the same or different.

Because of the nature of some of the defenses resulting from the various layers present in endospores, the composition must include at least one oxidizing acid. Many oxyacids, such as perchloric, chloric, chlorous, hypochlorous, persulfuric, sulfuric, sulfurous, hyposulfurous, pyrosulfuric, disulfurous, thiosulfurous, pernitric, nitric, nitrous, hyponitrous, perchromic, chromic, dichromic, permanganic, manganic, perphosphoric, phosphoric, phosphorous, hypophosphorus, periodic, iodic, iodous, etc., are considered to be oxidizing acids. Organic oxidizing acids include, but are not limited to, peracetic acid, peroxalic acid and diperoxalic acid.

Preferred oxidizing acids are those which have relatively high $pK_a$ values (i.e., are not considered to be particularly strong acids) and positive standard potentials ($E^0_{red}$). The former permits production of a composition that has a pH value that is not too low, i.e., below ~1.5, preferably not below ~1.75, more preferably not below ~2, and most preferably not below ~2.2, so that the composition can be used without extreme protective measures by those charged with handling and applying them to surfaces and/or destroying components of articles to be treated. A positive standard potential permits the acid to have sufficient oxidizing capacity to permit overcoming or avoidance of certain endospore defenses such as, for example, oxidation of disulfide linkages and protein polymers on the endospore coat, which allows the outer spore coat to be breached.

Preferred $pK_a$ values are greater than ~1, greater than ~1.5, greater than ~2, greater than ~2.5, greater than ~3, greater than ~3.5, greater than ~4, greater than ~4.5, greater than ~5, and even greater than ~5.5. Acids with lower $pK_a$ values can be used if other steps are taken to ensure compliance with required or desired properties of the composition such as pH range (discussed above) and effective solute concentration (discussed below).

Preferred $E^0_{red}$ values are those which are at least +0.20 V, at least +0.25 V, at least +0.33 V, at least +0.40 V, at least +0.50 V, at least +0.60 V, at least +0.67 V, at least +0.75 V, at least +0.80 V, at least +0.90 V, at least +1.00 V, at least +1.10 V, at least +1.20 V, or even at least +1.25 V.

Some oxidizing acids are not particularly stable in aqueous solutions. Accordingly, providing a composition with an oxidizing acid prepared in vitro can be advantageous. For example, in one preferred embodiment, to a solvent component of a composition can be provided acetic acid and hydrogen peroxide which, when contacted, reversibly form peracetic acid.

The amount of any given acid employed can be determined from the target pH of a given composition and the $pK_a$ value(s) of the chosen acids in view of the type and amounts of compound(s), if any, utilized to achieve the desired effective solute concentration in the composition. (More discussion of osmolarity and the types of osmolarity-adjusting compounds appears below.)

Also present in the solute component of the composition is an electrolyte oxidizing agent that does not contain any active hydrogen atoms when subjected to a Zerewitinoff determination. Non-limiting examples of potentially useful electrolyte, preferably inorganic, oxidizing agents include compounds which include anions such as manganate, permanganate, peroxochromate, chromate, dichromate, peroxymonosulfate, and the like. (Some of these electrolytes can impact pH, so a composition formulated to have a given pH might require adjustment after addition of the oxidizing agent(s).) Preferred are those compounds having $E^0_{red}$ values of at least +1.25 V, preferably at least +1.5 V, more preferably at least +1.75 V, even more preferably at least +2.0 V and most preferably at least +2.25 V.

Electrolyte oxidizing agents generally can be added at up to their individual solubility limits, although the maximum amount generally is on the order of 30 g per liter of total composition. Exemplary ranges of electrolyte oxidizing agent(s) are ~2 to ~25 g/L, ~3 to ~21 g/L, ~4 to ~18 g/L, ~5 to ~16 g/L and ~6 to ~14 g/L. Exemplary amounts of electrolyte oxidizing agent(s) are 17.5±12 g/L, 15±9 g/L, 12.5±6 g/L and 10±3 g/L.

Once the acid(s) and oxidizing agent(s) are added to a solvent component that contains water (or vice versa), each at least partially dissociates.

A composition that includes only a solvent component and a solute component that consists, or consists essentially of, one or more oxidizing acids and one or more electrolyte oxidizing agents can have efficacy against endospores, i.e., can result in some or all endospores being rendered incapable of returning to a vegetative state. Nevertheless, a composition that includes a solute component which includes additional subcomponents can have enhanced efficacy in certain circumstances.

In certain embodiments, the effective solute concentration of the composition can be relatively high. Often, efficacy increases as effective solute concentration (osmolarity) increases. The presence of an abundance of solutes ensures that a sufficient amount are present to induce a high osmotic pressure across the cortical membrane, leading to lysis.

This efficacy is independent of the particular identity or nature of individual compounds of the solute component, although smaller molecules are generally more effective than larger molecules due to solvent capacity (i.e., the ability to (typically) include more small molecules in a given amount of solvent component than an equimolar amount of larger molecules) and ease of transport across cortical membranes.

Any of a number of solutes can be used to increase the composition osmolarity.

One approach to achieving increased osmolarity of the composition is by adding large amounts of non-oxidizing electrolytes, particularly ionic compounds (salts); see, e.g., U.S. Pat. No. 7,090,882. Like the oxidizing acid and inorganic oxidizing agent, non-oxidizing electrolytes dissociate upon being introduced into a solvent component that includes water.

Where one or more organic acids are used in the composition, another approach to increasing osmolarity without increasing the pH of the composition past a desired target involves inclusion of salt(s) of one or more the acid(s) or the salt(s) of one or more other organic acids. Such compounds, upon dissociation, increase the effective amount of solutes in the composition without greatly impacting the molar concentration of hydronium ions while, simultaneously, providing a buffer system in the composition.

For example, where the composition includes an acid, a fraction up to a many fold excess (e.g., 3× to 10×, at least 5× or even at least 8×) of one or more salts of that (or another) acid also can be included. The identity of the countercation portion of the salt is not believed to be particularly critical, with common examples including ammonium ions and alkali metals. Where a polyacid is used, all or fewer than all of the H atoms of the carboxyl groups can be replaced with cationic atoms or groups, which can be the same or different. For example, mono-, di- and trisodium citrate all constitute potentially useful buffer precursors, whether used in conjunction with citric acid or another organic acid. However, because trisodium citrate has three available basic sites, it has a theoretical buffering capacity up to 50% greater than that of disodium citrate (which has two such sites) and up to 200% greater than that of sodium citrate (which has only one such site).

Regardless of how achieved, the effective solute concentration of the composition is at least 1.0 Osm/L, generally at least 1.25 Osm/L, often at least 1.5 Osm/L, commonly at least 1.75 Osm/L, more commonly at least 2.0 Osm/L, typically at least 2.25 Osm/L, more typically at least 2.5 Osm/L. (As points of comparison, in biological applications, a 0.9% (by wt.) saline solution, which is ~0.3 Osm/L, typically is considered to be have moderate tonicity, while a 3% (by wt.) saline solution, which is ~0.9 Osm/L, generally is considered to be hypertonic.) In some embodiments, the composition has an effective solute concentration of at least ~3.0, at least ~3.25, at least ~3.5, at least ~3.75, or even at least ~4.0 Osm/L, with the upper limit being defined by the solubility limit of the solutes in the solvent component; in some embodiments, the upper limit of effective solute concentration can range as high as 4.5, 4.75, 5.0, 5.25, 5.5, 5.75, 6.0, 6.25, 6.5, 6.75, 7.0, 7.2, 7.4, 7.6, 7.8, 8.0, 8.2, 8.4, 8.6, 8.8 or even ~9 Osm/L. Effective solute concentration ranges involving combinations of any of the lower and upper limits set forth in this paragraph also are envisioned. The effective solute concentrations of compositions according to the present invention, which are intended to be effective against (i.e., lethal to) endospores, generally are higher than those described in U.S. Pat. Nos. 8,940,792 and 9,314,017 as well as U.S. Pat. Publ. Nos. 2010/0086576, 2013/0272922, 2013/0079407 and 2016/0073628, all of which are directed generally against planktonic bacteria and biofilms.

Effective solute concentration can be calculated using known techniques or, if desired, measured using any of a variety of colligative property measurements such as boiling point elevation, freezing point depression, osmotic pressure and lowering of vapor pressure.

Unlike many of the compositions described in the documents listed in the preceding paragraph, the present sporicidal composition does not require inclusion of surfactant in the solute component, although certain preferred embodiments include one or more wetting agents which include, but are not limited to, surfactants.

Essentially any material having surface active properties in water can be employed, regardless of whether water is present in the solvent component of the composition, although those surface active agents that bear some type of ionic charge are expected to have enhanced antimicrobial efficacy because such charges, when brought into contact with a bacteria, are believed to lead to more effective bacterial membrane disruption and, ultimately, to cell leakage and lysis.

Polar surfactants generally are more efficacious than non-polar surfactants, with ionic surfactants being most effective. For polar surfactants, anionic surfactants generally are the most effective, followed by zwitterionic and cationic surfactants, with smaller molecules generally being preferred over larger ones. The size of side-groups attached to the polar head can influence the efficacy of ionic surfactants, with larger size-groups and more side-groups on the polar head potentially decreasing the efficacy of surfactants.

Potentially useful anionic surfactants include, but are not limited to, ammonium lauryl sulfate, dioctyl sodium sulfosuccinate, perflourobutanesulfonic acid, perfluorononanoic acid, perfluorooctanesulfonic acid, perfluorooctanoic acid, potassium lauryl sulfate, sodium dodecylbenzenesulfonate, sodium laureth sulfate, sodium lauroyl sarcosinate, sodium myreth sulfate, sodium myreth sulfate, sodium pareth sulfate, sodium stearate, sodium chenodeoxycholate, N-lauroylsarcosine sodium salt, lithium dodecyl sulfate, 1-octanesulfonic acid sodium salt, sodium cholate hydrate, sodium deoxycholate, sodium dodecyl sulfate (SDS), sodium glycodeoxycholate, sodium lauryl sulfate (SLS), and the alkyl phosphates set forth in U.S. Pat. No. 6,610,314. SLS is a particularly preferred material.

Potentially useful cationic surfactants include, but are not limited to, cetylpyridinium chloride (CPC), cetyl trimethylammonium chloride, benzethonium chloride, 5-bromo-5-nitro-1,3-dioxane, dimethyldioctadecylammonium chloride, cetrimonium bromide, dioctadecyldimethylammonium bromide, tetradecyltrimethyl ammonium bromide, benzalkonium chloride (BK), hexadecylpyridinium chloride monohydrate and hexadecyltrimethylammonium bromide.

Potentially useful nonionic surfactants include, but are not limited to, sodium polyoxyethylene glycol dodecyl ether, N-decanoyl-N-methylglucamine, digitonin, n-dodecyl ß-D-maltoside, octyl ß-D-glucopyranoside, octylphenol ethoxylate, polyoxyethylene (8) isooctyl phenyl ether, polyoxyethylene sorbitan monolaurate, and polyoxyethylene (20) sorbitan cholamidopropyl) dimethylammonio]-2-hydroxy-1-propane sulfonate, 3-[(3-cholamidopropyl) dimethylammonio]-1-propane sulfonate, 3-(decyldimethylammonio) propanesulfonate inner salt, and N-dodecyl-N,N-dimethyl-3-ammonio-1-propanesulfonate.

Potentially useful zwitterionic surfactants include sulfonates (e.g. 3-[(3-cholamidopropyl)dimethylammonio]-1-propanesulfonate), sultaines (e.g. cocamidopropyl hydroxysultaine), betaines (e.g. cocamidopropyl betaine), and phosphates (e.g. lecithin).

For other potentially useful materials, the interested reader is directed to any of a variety of other sources including, for example, U.S. Pat. Nos. 4,107,328, 6,953,772, 7,959,943, and 8,940,792.

The amount(s) of wetting agent(s) to be added to the composition is limited to some extent by the target effective solute concentration and compatibility with other subcomponents of the solute component of the composition. The total amount of wetting agent present in the composition can range from at least 0.1%, from at least 0.25%, from at least 0.5%, from at least 0.75% or from at least 1% up to 5%, commonly up to 4%, more commonly up to 3%, and typically up to 2.5%. At times, maximum amounts of certain types of wetting agents, particularly surfactants, that can be present in a composition for a particular end use (without specific testing, review and approval) are set by governmental regulations.

If more than one type of surfactant is employed, the majority preferably is an ionic surfactant, with the ratio of ionic-to-nonionic surfactant generally ranging from ~2:1 to ~10:1, commonly from ~5:2 to ~15:2, and typically from ~3:1 to ~7:1. Additionally, as is known in the art, a composition should not include surfactant types that are incompatible, e.g., anionic with cationic or zwitterionic with either anionic or cationic.

The antimicrobial composition can include a variety of additives and adjuvants to make it more amenable for use in a particular end-use application with negatively affecting its efficacy in a substantial manner. Examples include, but are not limited to, emollients, fungicides, fragrances, pigments, dyes, defoamers, foaming agents, flavors, abrasives, bleaching agents, preservatives (e.g., antioxidants) and the like. A comprehensive listing of additives approved by the U.S. Food and Drug Administration is available as a zipped text file at https://www.fda.gov/media/72482/download (link active as of filing date of this application).

The composition's efficacy does not require the inclusion of an active antimicrobial agent (defined above) for efficacy, but such materials can be included in certain embodiments. Non-limiting examples of potentially useful active antimicrobial additives include $C_2$-$C_8$ alcohols (other than or in addition to any used as an organic liquid of the solvent component) such as ethanol, n-propanol, and the like; aldehydes such as gluteraldehyde, formaldehyde, and o-phthalaldehyde; formaldehyde-generating compounds such as noxythiolin, tauroline, hexamine, urea formaldehydes, imidazolone derivatives, and the like; anilides, particularly triclocarban; biguanides such as chlorhexidine and alexidine, as well as polymeric forms such as poly(hexamethylene biguanide); dicarboximidamides (e.g., substituted or unsubstituted propamidine) and their isethionate salts; halogen atom-containing or releasing compounds such as bleach, $ClO_2$, dichloroisocyanurate salts, tosylchloramide, iodine (and iodophors), and the like; silver and silver compounds such as silver acetate, silver sulfadiazine, and silver nitrate; phenols, bisphenols and halophenols (including hexachlorophene and phenoxyphenols such as triclosan); and quaternary ammonium compounds.

The following tables provide ingredient lists for exemplary compositions according to the present invention, with amounts being provided in grams and with distilled water being added to bring the ingredients to a volume of 1 L.

TABLE 4

Formulations for exemplary compositions

|  | Formulation 1 | Formulation 2 |
|---|---|---|
| salt of organic acid | 5-25 | 10-20 |
| organic acid | 125-200 | 140-180 |
| ionic surfactant | 5-30 | 15-25 |
| nonionic surfactant | 0-5 | 1-3 |
| $H_2O_2$ (30% by wt. in $H_2O$) | 175-325 | 200-300 |
| inorganic oxidizing agent | 4-20 | 6-12 |
| organic liquid | 175-450 | 225-375 |

Various embodiments of the present invention have been provided by way of example and not limitation. As evident from the foregoing tables, general preferences regarding features, ranges, numerical limitations and embodiments are, to the extent feasible and as long as not interfering or incompatible, envisioned as being capable of being combined with other such generally preferred features, ranges, numerical limitations and embodiments.

A composition according to the present invention is intended to be, and in practice is, aggressively antimicrobial. Its intended usages are in connection with inanimate objects such as, in particular, hard surfaces, particularly those commonly found in healthcare facilities.

The composition can be applied to inanimate objects, particularly hard surfaces, in a variety of ways including pouring, spraying or misting, via a distribution device (e.g., mop, rag, brush, textile wipe, etc.), and the like.

Alternatively, certain objects are amenable to being immersed in a composition. This is particularly true of medical equipment designed for use with multiple patients such as, for example, dialysis equipment, any of a variety of endoscopes, duodenoscopes, etc., endoscopic accessories such as graspers, scissors and the like, manual instruments such as clamps and forceps, laparoscopic surgical accessories, orthopedic and spinal surgery hardware such as clamps and jigs, and the like. Because the composition of the present invention has a more moderate [$H^+$] than treatments such as peracetic acid and bleach, it can achieve disinfection, high level disinfection or even sterilization without negative effects such as, e.g., polymeric degradation, metal corrosion, glass or plastic etching, and the like.

Once applied to a surface or object, the various ingredients of the composition act on any endospores present and avoid or break down their various defenses. The contact time necessary for a composition to treat endospores (i.e., ensure that they cannot return to a vegetative state) can vary widely depending on the particular composition and its intended end use.

For example, embodiments of a composition intended to be applied to hard surfaces in a healthcare facility can achieve at least a 3.0, 3.2, 3.4, 3.6, 3.8, 4.0, 4.2, 4.4, 4.6, 4.8 or 5.0 log reduction after a contact time of more than 1200 seconds, no more than 1050 seconds, no more than 900 seconds, no more than 840 seconds, no more than 780 seconds, no more than 720 seconds, no more than 660 seconds, or even no more than 600 seconds. When tested in accordance with ASTM E2197-11, certain embodiments can achieve at least a 4.5 log reduction after a contact time of 600 seconds.

These and/or other embodiments of a composition intended for use as a soaking bath for medical devices can achieve at least a 5.0, 5.1, 5.2, 5.3, 5.4, 5.5, 5.6, 5.7, 5.8, 5.9, or 6.0 log reduction after a contact time of ~14,400 seconds, up to ~10,800 seconds, up to ~7200 seconds, up to ~5400 seconds, and on the order of ~3600 seconds. When tested in accordance with AOAC Official Method 966.04, certain embodiments can achieve a passing score after contact times as low as 1800 seconds.

Embodiments of the sporicidal composition may be able to be classified as high level disinfectants or even as sterilants.

After the composition has been allowed to contact a given object or surface for an appropriate time (in view of factors such as expected bacterial load, type of bacteria potentially present, importance of the object/surface, etc.), it can be left to evaporate or, preferably, rinsed away with water or a dilute saline solution.

The following non-limiting, illustrative examples provide detailed conditions and materials that can be useful in the practice of the present invention. Throughout those examples, any reference to room temperature refers to ~22° C.

EXAMPLES

Example 1 (Comparative)

Peracetic Acid

A widely recognized and recommended disinfection treatment where endospores are possible or suspected is application to the target surface and 10 minute contact time of 10% (w/v) peracetic acid. Accordingly, peracetic acid constitutes a good comparative for compositions of the present invention.

Two peracetic acid solutions were prepared by adding distilled water to a flask containing peracetic acid. The concentration of one of the solutions was 5% (w/v) while that of the other was 10% (w/v). The calculated effective solute concentrations for these solutions were 1.97 and 3.95 Osm/L, respectively.

To a 50 mL beaker was added 20 mL distilled water. A cleaned, rinsed and dried probe from a calibrated, temperature compensating pH meter was lowered into the beaker. Sequential aliquots of the peracetic acid solution then were added to the beaker, with pH readings after each. The titrations were performed at room temperature.

The results of these titrations are shown below in Table 5.

TABLE 5

Peracetic acid titrations

| 5% (w/v) | | 10% (w/v) | |
|---|---|---|---|
| Amt. acid, mL | pH | Amt. acid, mL | pH |
| 0 | 5.91 | 0 | 5.31 |
| 0.25 | 2.42 | 0.1 | 2.74 |
| 0.50 | 2.17 | 0.2 | 2.48 |
| 0.75 | 2.00 | 0.3 | 2.33 |
| 1.00 | 1.89 | 0.4 | 2.22 |
| 1.25 | 1.80 | 0.5 | 2.14 |
| 1.50 | 1.74 | 0.6 | 2.07 |

TABLE 5-continued

Peracetic acid titrations

| 5% (w/v) | | 10% (w/v) | |
|---|---|---|---|
| Amt. acid, mL | pH | Amt. acid, mL | pH |
| 1.75 | 1.68 | 0.7 | 2.00 |
| 2.00 | 1.59 | 0.8 | 1.95 |
| 2.25 | 1.56 | 0.9 | 1.91 |
| 2.50 | 1.53 | 1.0 | 1.86 |
| 2.75 | 1.48 | 1.1 | 1.83 |
| 3.00 | 1.45 | 1.2 | 1.79 |
| 3.25 | 1.42 | 1.3 | 1.76 |
| 3.50 | 1.41 | 1.4 | 1.73 |
| 3.75 | 1.38 | 1.5 | 1.70 |
| 4.00 | 1.34 | 1.6 | 1.67 |
| 4.25 | 1.30 | 1.7 | 1.65 |
| 4.50 | 1.28 | 1.8 | 1.62 |
| 4.75 | 1.26 | 1.9 | 1.60 |
| 5.00 | 1.25 | 2.0 | 1.58 |

The above data indicate, inter alia, that the pH of water is reduced to below 3 upon addition of even a tiny aliquot, i.e., less than 1% by volume, of either peracetic acid solution and that the addition of only 1 mL (5% by volume) of either solution has reduced the pH to below 2. Further, the asymptotic pH for either acid solution is on the order of 1.1±0.1.

Further, U.S. EPA recommendations are for peracetic acid solutions of at least 2.5% (w/v) which, according to the tabulated data, has a pH of no more than 1.25.

Thus, any worker performing this recommended disinfection procedure (i.e., application of a 2.5-10% peracetic acid solution) should employ the types of precautions appropriate for handling strong acids such as, e.g., protective gloves, protective eyewear, breathing masks, etc.

Example 2 (Comparative)

Bleach

Another widely recognized and recommended disinfection treatment where endospores are possible or suspected is application to the target surface and 10 minute contact time of a bleach solution.

To a 50 mL beaker was added 5 mL of a bleach solution, i.e., 8.25% (w/v) sodium hypochlorite. A cleaned, rinsed and dried probe from a calibrated, temperature compensating pH meter was lowered into the beaker. Sequential aliquots of distilled water then were added to the beaker, with pH readings after each.

The data from this titration are shown below in Table 6.

TABLE 6

Titration of household bleach with water

| Water, mL | [ClO⁻], % (w/v) | pH |
|---|---|---|
| 0 | 8.25 | 12.56 |
| 2 | 5.89 | 12.46 |
| 4 | 4.58 | 12.33 |
| 6 | 3.75 | 12.23 |
| 8 | 3.17 | 12.14 |
| 10 | 2.75 | 12.06 |
| 12 | 2.43 | 12.00 |
| 14 | 2.17 | 11.94 |
| 16 | 1.96 | 11.89 |
| 18 | 1.79 | 11.84 |
| 20 | 1.65 | 11.79 |

TABLE 6-continued

Titration of household bleach with water

| Water, mL | [ClO⁻], % (w/v) | pH |
|---|---|---|
| 22 | 1.53 | 11.74 |
| 24 | 1.42 | 11.70 |
| 25 | 1.38 | 11.68 |

The data of this table indicate, inter alfa, that an undiluted 8.25% bleach solution has a pH of almost 13 and that reducing the ClO⁻ concentration by three-fourths reduces this only to ~11.9. Conversely, reducing the concentration from 8.25% to 5% (both w/v) results in the calculated effective solute concentration being reduced by almost half, i.e., from 2.28 to 1.34 Osm/L.

Thus, any worker performing this recommended disinfection procedure (i.e., application of a bleach solution) should employ the types of precautions appropriate for handling strong bases, e.g., protective gloves, protective eyewear, breathing masks, etc.

Examples 3-10

In Vitro Time-to-Kill

Efficacy of certain sporicidal compositions was performed against *Clostridium difficile* (ATCC #43598). In this testing, reduction of bacteria is determined by comparison against untreated controls (employing phosphate buffered saline as liquid) at various time test points, typically equal increments such as 15 minutes (900 seconds).

A 9.9 mL aliquot of the solution to be tested was placed in a 20 mL test tube. A 0.1 mL volume of the test culture (~$10^6$ colony forming units (CFU) of *C. Diff* per mL when diluted) was added to the test tube, which then was vortexed. After a predetermined amount of contact time, 1.0 mL of the sample/test culture suspension was transferred into sterile test tubes containing 9.0 mL of an appropriate neutralization solution, followed by additional vortexing.

Serial tenfold dilutions then were prepared by transferring 0.5 mL aliquots of test solution into 4.5 mL of neutralizing solution, with vortex mixing between dilutions. From these dilutions, duplicate 1.0 mL aliquots were spread-plated onto brain-heart agar plates, which then were incubated anaerobically at 35°±2° C. for ~72 hours.

Following incubation, the colonies on the plates were counted, with counts in the 20 to 200 CFU range used in data calculations. The log reduction from this testing is performed by subtracting the CFU/mL recovered treatment value from the CFU/mL recovered control sample.

A number of compositions were tested in this manner, with the time to achieve 6 log reductions in spores shown in the last column of Table 7 below. Each of the compositions was prepared based on a targeted ~2.3 Osm/L effective solute concentration and a target pH of 4. (In the buffer system column, "A" represents acetic acid/sodium acetate, while "C" represents citric acid/trisodium citrate. In the oxidant column, "PPOMS" represents peroxymonosulfate, all at 0.22% (w/v), and "PAA" represents peracetic acid at the noted concentration.) Those compositions designated as employing BK as a surfactant included 0.21% (w/v), while those designated as employing SDS included 0.175% (w/v). For those compositions showing inclusion of an organic liquid, an isopropanol solution (70% in water) was employed.

TABLE 7

| Example | Buffer system | Oxidant | Surfactant | Org. liquid (%, w/v) | Time (min.) |
|---|---|---|---|---|---|
| 3 | A | PPOMS | BK | — | 30 |
| 4 | A | PPOMS | SDS | — | 30 |
| 5 | A | PPOMS | BK | 10.0 | 60 |
| 6 | C | PAA (0.1%) | BK | 20.0 | 30 |
| 7 | C | PAA (1.0%) | BK | 20.0 | 30 |
| 8 | A | PPOMS | BK | — | 30 |
| 9 | A | PPOMS | SDS | — | 30 |
| 10 | A | PPOMS | SDS | 10.0 | 15 |

The times shown in the foregoing table are better than those which can be achieved with most commercially available sporicidal products, which typically require 240 to 2160 minutes for *C. Diff* disinfection. Additionally, exposure to each of these compositions is far less dangerous than exposure to such commercial products.

Examples 11-22

The data from Table 7 above seem to indicate that compositions employing an anionic surfactant (SDS) might provide better results than those employing a cationic surfactant (BK).

To further investigate efficacy, additional compositions were prepared, each of which employed the same amount of SDS as was used in Examples 4 and 9-10 plus 0.02% (w/v) of a polysorbate-type nonionic surfactant. Each also included 250 g/L of a 30% $H_2O_2$ solution and 300 g/L of an organic liquid. The electrolyte oxidizing agent (EOA) for each composition was PPOMS. The citric acid-containing compositions included 140 g/L citric acid and 17.5 g/L trisodium citrate dihydrate (along with the noted amounts of NaCl to raise the effective solute concentration to a predetermined target), while the acetic acid-containing compositions included the noted amounts of acetic acid (AA) and sodium acetate (SA).

Quantitative carrier testing was performed in substantial accord with ASTM standard E2197-11, with efficacy against spores being shown in the last columns of the following tables.

TABLE 8a citric acid compositions

| Example | Target pH | Amt. NaCl (g/L) | Amt. EOA (g/L) | Organic liquid | Log reduction |
|---|---|---|---|---|---|
| 11 | 1.5 | 54.0 | 12.0 | IPA | 5.6 |
| 12 | 3.5 | 54.0 | 4.0 | IPA | 3.2 |
| 13 | 1.5 | 178.2 | 12.0 | DGME | <3 |
| 14 | 3.5 | 178.2 | 4.0 | DGME | <3 |
| 15 | 2.5 | 116.0 | 8.0 | DGME | 3.9 |
| 16 | 2.5 | 116.0 | 8.0 | IPA | 3.9 |

TABLE 8b acetic acid compositions

| Example | Target pH | Amts. AA/SA (g/L) | Amt. EOA (g/L) | Organic liquid | Log reduction |
|---|---|---|---|---|---|
| 17 | 1.5 | 82.4/7.4 | 4.0 | DGME | 5.0 |
| 18 | 3.5 | 82.4/7.4 | 12.0 | DGME | 3.3 |
| 19 | 1.5 | 164.9/14.8 | 4.0 | IPA | 5.1 |
| 20 | 3.5 | 164.9/14.8 | 12.0 | IPA | 4.7 |
| 21 | 2.5 | 123.6/11.1 | 8.0 | DGME | 5.3 |
| 22 | 2.5 | 123.6/11.1 | 8.0 | IPA | 5.0 |

Statistical analysis of the data from these tables suggested that the type of acid has the greatest impact on efficacy followed by, in order, the pH (lower being better), type of solvent, and effective solute concentration. The amount of electrolyte oxidizing agent appears to have a lesser effect.

Examples 23-31

Using Example 22 as a center point (rerun below as Example 23), additional quantitative carrier tests were conducted on another round of prepared compositions in which the targeted pH (2.5), effective solute concentration (~6.4 Osm/L) and amount of PPOMS (8 g/L) were held constant. The anionic surfactant was SDS, while the nonionic surfactant was a polysorbate. The organic liquid for each was a 70% (v/v) IPA solution.

TABLE 9

| Example | Org. liquid (g/L) | $H_2O_2$ soln. (g/L) | Anionic surf. (g/L) | Nonionic surf. (g/L) | Log reduction |
|---|---|---|---|---|---|
| 23 | 250 | 250 | 17.5 | 2.0 | 4.6 |
| 24 | 200 | 200 | 15.0 | 1.5 | 4.6 |
| 25 | 400 | 300 | 15.0 | 1.5 | 4.7 |
| 26 | 200 | 300 | 20.0 | 1.5 | 4.6 |
| 27 | 400 | 200 | 20.0 | 1.5 | 4.6 |
| 28 | 200 | 300 | 15.0 | 2.5 | 4.7 |
| 29 | 400 | 200 | 15.0 | 2.5 | 4.6 |
| 30 | 200 | 200 | 20.0 | 2.5 | 4.5 |
| 31 | 400 | 300 | 20.0 | 2.5 | 4.7 |

Analysis of the data for Examples 11-31 indicated that pH and type of acid had the greatest impact, followed by effective solute concentration and type of solvent.

Examples 32-40

Additional quantitative carrier testing was performed on compositions in which the pH (2.5) and effective solute concentration (~6.4 Osm/L) were held constant. This set varied the amount of electrolyte oxidizing agent (PPOMS), the amount and type of solvent (with E representing absolute ethanol), the amount of hydrogen peroxide solution, and the amounts of anionic (SDS) and nonionic (polysorbate-type) surfactants.

TABLE 10

| Example | Org. liquid (g/L) | $H_2O_2$ soln. (g/L) | PPOMS (g/L) | Anionic surf. (g/L) | Nonionic surf. (g/L) | Log reduction |
|---|---|---|---|---|---|---|
| 32 | E, 250 | 200 | 12 | 15.0 | 1.5 | 4.7 |
| 33 | E, 250 | 300 | 20 | 15.0 | 1.5 | 4.7 |
| 34 | DGME, 250 | 300 | 12 | 20.0 | 1.5 | 4.5 |
| 35 | DGME, 250 | 200 | 20 | 20.0 | 1.5 | 3.9 |
| 36 | E, 350 | 300 | 12 | 15.0 | 2.5 | 3.8 |
| 37 | E, 350 | 200 | 20 | 15.0 | 2.5 | 4.5 |
| 38 | DGME, 350 | 200 | 12 | 20.0 | 2.5 | 4.6 |
| 39 | DGME, 350 | 300 | 20 | 20.0 | 2.5 | 4.7 |
| 40 | IPA, 300 | 250 | 16 | 17.5 | 2.0 | 4.7 |

Analysis of this data suggests that, when type and amount of acid is held constant, the most statistically significant factors might be two-way combinations type of solvent, solvent concentration, and amount of electrolyte oxidizing agent.

That which is claimed is:

1. A sporicidal composition having a pH of from 1.65 to 3.75, inclusive, and a calculated effective solute concentration of at least 3 Osm/L, said composition comprising, on a per liter basis:
   a) a solvent component having a $\delta_p$ value no more than 15.2 MPa$^{1/2}$ that comprises
      1) 50 to 500 mL water and
      2) from 175 to 450 g of at least one organic liquid, and
   b) a solute component that comprises
      1) dissociation products of an oxidizing acid having a pK$_a$ value of greater than 3 and a standard potential of at least +0.5 V,
      2) dissociation products of from 4 to 20 g of an electrolyte oxidizing agent having a standard potential of at least +1.5 V, and
      3) dissociation products of at least one salt of an organic acid.

2. The sporicidal composition of claim 1 wherein said solute component further comprises wetting agent.

3. The sporicidal composition of claim 2 wherein said wetting agent comprises anionic surfactant.

4. The sporicidal composition of claim 3 wherein said wetting agent further comprises nonionic surfactant.

5. The sporicidal composition of claim 4 wherein said solute component comprises dissociation products of 12.5±6 g of said electrolyte oxidizing agent.

6. The sporicidal composition of claim 4 wherein said electrolyte oxidizing agent has a standard potential of at least +2.0 V.

7. The sporicidal composition of claim 6 wherein said solute component comprises dissociation products of 12.5±6 g of said electrolyte oxidizing agent.

8. The sporicidal composition of claim 1 wherein said oxidizing acid is the reaction product of an organic acid and a peroxide.

9. The sporicidal composition of claim 1 having a pH of no more than 3.

10. The sporicidal composition of claim 1 wherein said electrolyte oxidizing agent has a standard potential of at least +2.0 V.

11. The sporicidal composition of claim 10 wherein said solute component comprises 12.5±6 g of said electrolyte oxidizing agent.

12. The sporicidal composition of claim 1 having a pH of no more than 3.

13. The sporicidal composition of claim 1 wherein said at least one organic liquid comprises a glycol ether.

14. The sporicidal composition of claim 1 wherein said at least one organic liquid is a glycol ether.

15. The sporicidal composition of claim 1 wherein said solvent component has a $\delta_p$ value of from 13.5 to 15.5 MPa$^{1/2}$.

16. A sporicidal composition having a pH of from 1.65 to 3.75, inclusive, and a calculated effective solute concentration of at least 3 Osm/L, said composition comprising, on a per liter basis:
   a) a solvent component having a $\delta_p$ value no more than 15.2 MPa$^{1/2}$ that comprises
      1) 50 to 500 mL water and
      2) from 175 to 450 g of at least one organic liquid that comprises a glycol ether, and
   b) a solute component that comprises
      1) dissociation products of an oxidizing acid having a pK$_a$ value of greater than 3 and a standard potential of at least +0.5 V, 2) dissociation products of from 12.5±6 g of an electrolyte oxidizing agent having a standard potential of at least +1.5 V, 3) dissociation products of at least one salt of an organic acid, and
      4) wetting agent.

17. The sporicidal composition of claim 16 wherein said solvent component has a $\delta_p$ value of from 13.5 to 15.5 MPa$^{1/2}$.

18. The sporicidal composition of claim 16 wherein said at least one organic liquid is a glycol ether.

19. The sporicidal composition of claim 16 wherein said wetting agent comprises anionic surfactant and optionally a nonionic surfactant.

20. The sporicidal composition of claim 16 wherein said electrolyte oxidizing agent has a standard potential of at least +2.0 V.

* * * * *